United States Patent [19]
Goken et al.

[11] Patent Number: 5,891,559
[45] Date of Patent: Apr. 6, 1999

[54] SOLID PHASE EXTRACTION USING COMPOSITE SHEET FOR DIRECT MEASUREMENT OF RADIOACTIVITY

[75] Inventors: Garold L. Goken, Birchwood; Wolfgang H. Strehlow, St. Paul, both of Minn.

[73] Assignee: Minnesota Mining and Manufacturing Co., St. Paul, Minn.

[21] Appl. No.: 921,552

[22] Filed: Sep. 2, 1997

Related U.S. Application Data

[60] Continuation of Ser. No. 449,375, May 23, 1995, abandoned, which is a division of Ser. No. 337,081, Nov. 11, 1994, Pat. No. 5,637,506.

[51] Int. Cl.⁶ ........................................................ B32B 5/14
[52] U.S. Cl. ..................... 428/220; 428/317.9; 442/325; 442/326; 442/417; 427/212
[58] Field of Search ................................ 428/220, 317.9; 442/325, 326, 417; 427/212

[56] References Cited

U.S. PATENT DOCUMENTS

| | | | |
|---|---|---|---|
| 2,985,758 | 5/1961 | Bosch | 250/383 |
| 3,316,066 | 4/1967 | Smit | 423/2 |
| 3,409,771 | 11/1968 | Riel | 250/343 |
| 3,825,410 | 7/1974 | Bagshawe | 23/230 R |
| 3,967,932 | 7/1976 | Sano et al. | 23/230 R |
| 4,142,020 | 2/1979 | Okamura et al. | 428/403 |
| 4,153,661 | 5/1979 | Ree et al. | 264/120 |
| 4,460,474 | 7/1984 | Blasius et al. | 210/679 |
| 4,683,124 | 7/1987 | Muscatello et al. | 423/6 |
| 4,880,984 | 11/1989 | Shiraishi | 250/484 |
| 4,943,375 | 7/1990 | Bradshaw et al. | 210/674 |
| 5,071,610 | 12/1991 | Hagen et al. | 264/120 |
| 5,124,041 | 6/1992 | Sheer et al. | 210/641 |
| 5,279,742 | 1/1994 | Markell et al. | 210/638 |
| 5,328,758 | 7/1994 | Markell et al. | 428/281 |
| 5,344,624 | 9/1994 | Foos et al. | 423/6 |

FOREIGN PATENT DOCUMENTS

| | | |
|---|---|---|
| A 0 437287 | 7/1991 | European Pat. Off. . |
| A 1 420916 | 1/1976 | United Kingdom . |
| WO A93 01494 | 1/1993 | WIPO . |

OTHER PUBLICATIONS

"DOE Methods for Evaluating Environmental and Waste Management Samples," US DOE, RP–500, Mar. 1993.
Poziomek, E.J., "Solid State Extraction and Solid State Spectroscopy for Monitoring Water Polution," Analytical Letters, 24(10), 1913–1921 (1991).
3M Empore™ Extraction Disks, A New Standard for Sample Preparation (brochure) 1993.
3M Empore™ Extraction Disks, The Environmental Analysis Standard (brochure) 1993.
D. Eastwood, et al., "A Solid Phase Extraction/Solid State Luminescence Approach for Monitoring PAHs in Water," Analysis 22 (1994) 305–310.
S. I. Novik et al., Chem. Abstr., 1981, 95 140605n.
C. Kantipuly et al., Talanta 1990, 37, 491–517.
L. N. Moskvin et al., Chem. Abstr., 1992, 117, 263801d.

Primary Examiner—Marion McCamish
Assistant Examiner—Elizabeth M. Cole
Attorney, Agent, or Firm—Gary L. Griswold; Robert W. Sprague; William J. Bond

[57] ABSTRACT

A method of radiochemical analysis comprises the steps of providing a solid phase extraction sheet material comprising ion-specific sorptive or reactive particles and a porous matrix as carrier for the particles, and providing a fluid including an ion-containing radiochemical analyte comprising the specific ion, contacting the sheet material with the fluid for a time sufficient for the particles to selectively extract the analyte from the fluid, and analyzing the sheet material in a direct mode for quantitative or qualitative data relating to the radiochemical analyte. Solid phase extraction sheet materials and methods for their preparation are also disclosed.

31 Claims, No Drawings

SOLID PHASE EXTRACTION USING COMPOSITE SHEET FOR DIRECT MEASUREMENT OF RADIOACTIVITY

This is a continuation of application Ser. No. 08/449,375 filed May 23, 1995, now abandoned, which is a divisional of application Ser. No. 08/337,081 filed Nov. 11, 1994, now U.S. Pat. No. 5,637,506.

FIELD OF THE INVENTION

The present invention relates to direct quantitative or qualitative measurement of radioactivity emitted by a radioactive analyte sorbed or reacted in a composite solid phase extraction sheet material. In another aspect, a solid phase extraction sheet material capable of concentrating a radioactive analyte is disclosed.

BACKGROUND OF THE INVENTION

The U.S. Department of Energy faces one of the largest environmental challenges in the world. The Department's Environmental Restoration and Waste Management program has responsibility for identifying and reducing risks and managing waste at 137 sites in 34 states and territories where nuclear energy or weapons research and product resulted in radioactive and hazardous waste contamination.

Tests to quantify radionuclide contamination of soil, sediments, and groundwater will need to precede the remediation activities. Monitoring activities will continue even after completion of remediation activities. The number of radiochemical analyses being performed per year in the United States exceeds one million samples per year.

Radiochemical analyses involve specific isotopes or groups of isotopes. Tests are performed to determine quantities of radioisotopes of uranium, plutonium, cesium, radium, strontium, americium, iodine and a number of less frequently analyzed elements.

Radioactive strontium (isotopes $Sr^{89}$ and $Sr^{90}$) is one of the more frequent radionuclide contaminants found in groundwater or soils and sediments. Procedures for the analysis of strontium isotopes are documented in "DOE Methods for Evaluating Environmental and Waste Management Samples," U.S. Department of Energy, RP-500, March, 1993.

A common feature of all current radiochemical analyses is the labor-intensive nature of the tests, requiring the involvement of highly trained technicians. In the case of the analysis of radioactive strontium, the procedure involves one of several pre-concentration methods, a method to isolate and purify the Sr-fraction, and detection methods. Strontium is chemically separated from other sample constituents using a strontium selective chemical precipitation method. Repeated preconcentration, precipitation and extraction chromatography steps contribute to preparation time of several hours per sample. The use of columns of Sr-Spec™ extraction chromatography resin, supplied by Eichrom Industries, Inc., Darien, Ill., has somewhat simplified the isolation and purification of the Sr-fraction without substantially reducing the time required for the total analysis.

A solid phase extraction disk for use in direct analysis by solid-state luminescence has been described by E. J. Poziomek, "Solid State Extraction and Solid-State Spectroscopy for Monitoring Water Pollution," (Analytical Letters, 24(10), 913–1921 (1991). The extraction disk of the reference involves C-18 modified silica particles in a Teflon™ matrix.

U.S. Pat. No. 3,967,932 describes a method of analyzing cation-containing liquids in which a solution is passed through filter paper comprising fibers having cation-exchange functional groups. The cation-loaded filter paper is analyzed directly by, e.g., X-ray fluorescence spectroscopy, or the cation is eluted from the filter paper for subsequent analysis. Selectivity for specific cations is not described.

U.S. Patent Nos. 4,142,020, 4,460,474, and 4,943,375, 5,344,624, and others, relate to the selective removal of ions including, e.g., strontium, uranium, plutonium, cesium, or yttrium, from aqueous solutions containing other ions by means of solid phase extraction columns comprising crown ether derivatives coated on solid supporting media, or by means of liquid-liquid extraction using crown ether derivatives.

SUMMARY OF THE INVENTION

Briefly, the present invention provides a direct method of radiochemical analysis comprising the steps:

a) providing a solid phase extraction sheet material comprising ion-specific sorptive or reactive particles and a porous matrix as carrier for the particles, and providing a fluid including a radiochemical analyte comprising the specific ion, b) contacting the sheet material with the fluid for a time sufficient for the particles to selectively extract the analyte from the fluid, and c) analyzing the sheet material in a direct mode for quantitative or qualitative data relating to the radiochemical analyte.

Preferably, the sheet material is in disk form and preferably the analyte becomes concentrated in a surface band of the sheet material.

In another aspect, a solid phase extraction sheet material comprises a porous matrix having enmeshed therein ion-specific sorptive or reactive particles to which a radionuclide is physically or chemically bound.

In a further aspect, a solid phase extraction sheet material comprises a porous matrix on at least one surface of which is located ion-specific sorptive or reactive particles to which a radionuclide is physically or chemically bound.

In this application:

"direct mode" means measuring radioactivity emitted by at least one radionuclide sorbed or reacted into a sheet material without first separating the radionuclide(s) from other interfering radionuclides and without elution from the disk;

"disk" means a single layer of a solid phase extraction medium having a specified geometry;

"fluid" means liquid or gas;

"matrix" means an open-structured entangled mass of fibers or fibrils;

"particle" or "particulate" means a regular or irregularly shaped particle having an average size (largest diameter) in the range of 0.1 to 200 micrometers, preferably in the range of 0.1 to 30 micrometers, more preferably in the range of 1 to 20 micrometers; even more preferably in the range of 1 to 12 micrometers; and most preferably 1 to 10 micrometers;

"polymer pulp" means fibrids which are usually frazzled, i.e., in a frayed or tattered condition, having a high specific surface area, and a high adsorptive capacity for water;

"radionuclide" means a soluble, typically ionic, species of a radioisotope of an element; preferably the radionuclide is one of the elements uranium, plutonium, cesium, radium, strontium, americium, and iodine. For example, radioisotopes $U^{234}$, $U^{235}$ and $U^{238}$, $Pu^{238}$, $Pu^{239}$ and $Pu^{240}$, $Ra^{226}$ and $Ra^{228}$, $Am^{241}$ and $Am^{243}$, $Sr^{89}$ and $Sr^{90}$, $Cs^{134}$ and $Cs^{137}$, $I^{129}$ and $I^{131}$ can be analyzed by measuring their radioactive emissions;

"reactive" means capable of entering into a chemical reaction;

"sheet material" means a single layer of solid phase extraction medium or multiple superimposed layers of such media;

"solid phase extraction" (SPE) means a process employing a solid phase for extracting an ionic species from a fluid phase such as gases or liquids by sorptive, ion exchange, chelation, molecular size exclusion, etc., mechanisms; extracting can be by means of sorption or chemical reaction;

"sorptive" or "sorption" or "sorbent" means capable of taking up and holding by either absorption or adsorption; and "surface band" means the portion adjacent the face and penetrating into the sheet material or disk which first comes in contact with an analyte solution when the sheet is used in a "flow-through" or "immersion" SPE mode.

In one embodiment, sheet materials useful in the present invention can be provided by incorporating radionuclide-specific sorbent or reactive particles into at porous, preferably fibrous or fibrillated matrix to provide a composite sheet material as is disclosed, for example, in U.S. Pat. Nos. 4,153,661, 5,026,456 and 5,071,610, and Japanese Patent Kokai HEI3 [1991]-119200. Due to the radionuclide-specific extraction particles incorporated in the composite sheet material, disks manufactured from the composite sheet material sorb or react with isotopes of a given element without appreciably affecting isotopes of a different element in the fluid. The extracted isotopes of a given element typically are concentrated in a surface band of the sheet material because of the small size of the sorptive particles, high concentration of the sorptive particles, the high particle density of the sheet material, and the small pore size of the medium.

In another embodiment of the present invention, sheet materials can be provided by a process in which a fluid comprising insoluble ion-specific sorptive or reactive particles is passed through, or is allowed to soak into, a porous matrix so that the ion-specific sorptive or reactive particles become sorbed or reacted on at least one surface of the porous matrix which acts as a carrier for the particles. Alternatively, ion-specific sorptive or reactive particles can be wet- or dry-packed onto a surface of the porous matrix. In the process of the present invention, a radiochemical analyte comprising the specific ion can be physically or chemically bound to the sheet material.

The present invention offers significant advantages over known sample preparation methods. First, the disk provides for efficient extraction (less time, less processing, less skill required) of ions of a selected element without interference from ions of other elements. Second, the disks may be used to determine directly the alpha, beta, or gamma radiation count representative of the extracted radiochemical analytes.

DETAILED DESCRIPTION OF THE PREFERRED EMBODIMENTS

The sheet material of the present invention, which preferably is a disk, can be a composite sheet comprising a porous matrix which can be a fibrous nonwoven polymer such as polyolefin (e.g., polypropylene, polyethylene) and copolymers thereof, polyacrylonitrile, fibrillated polymer such as polytetrafluoroethylene (PTFE), nonwoven inorganic fibrous matrix such as glass or ceramic materials, or a fibrous polymer pulp or a blend of fibrous pulps such as those comprising aramids such as poly(p- or m-phenyleneterephthalamide) or chemical modifications thereof, optionally blended, for example, with polyolefin fibers, each with sorptive or reactive particles enmeshed therein.

In a more preferred embodiment, the present invention provides an article having a composite structure and method therefor, the composite structure preferably being an essentially uniformly porous, composite sheet comprised of non-water swellable sorptive or reactive particles distributed essentially uniformly throughout a matrix formed of intertangled, PTFE fibrils. In such a structure, almost all of the particles are separated one from another and each is isolated and not adhered one to another, or to a cage-like matrix, that restrains the particle on all sides by a fibrillated mesh of PTFE microfibers.

The preferred extraction sheet material of this invention, when it is a single layer of solid phase extraction medium or a disk, has a thickness in the range of 0.05 to 5.0 mm, and has a tensile strength of at least 100 KPa and even as high as 700 KPa.

In another embodiment, suitable pulps for providing the sheet materials of the present invention include aramid pulps, preferably poly(p-phenyleneterephthalamide) (Kevlar™, Dupont) and polyacrylonitrile (PAN) and derivatives thereof. Blends with polyolefin pulps, such as at least one of polypropylene and polyethylene, can be used to optimize the physical and sorptive properties of the sheet materials. Ratios of aramid pulps to polyolefin pulps can be in the range of 1 to 100 weight percent to 99 to 0 weight percent, preferably 10 to 90 weight percent to 90 to 10 weight percent.

Other fibrous pulps can comprise main fibers surrounded by many smaller attached fibrils, resulting in a high surface area material. The main fiber generally can have a length in the range of 0.8 mm to 4.0 mm, and an average diameter in the range of less than 1 to 20 micrometers, preferably less than 1 to 12 micrometers.

Sorptive or reactive particulate that can be incorporated in or on the sheet materials of the present invention include particles which interact by ion exchange, chelation, molecular size exclusion or sorption mechanisms to bind and remove ions from fluids in which they are dissolved. Such particles preferably are based upon derivatives of inorganic oxides such as silica, alumina, titania, and zirconia, having capability of sorbing or reacting with a specific radionuclide. Preferably, particles are inorganic oxide covalently bonded with a macrocyclic ligand, preferably silica bonded with a macrocyclic ligand, or a long-chain ligand, as disclosed for example in one or more of U.S. Pat. Nos. 4,943,375, 5,179,213, 5,244,856, and 5,084,430. Covalently bonded ligands include, for example, SuperLig™ 620, manufactured by IBC Advanced Technologies, Inc., Provo, Utah.

In one embodiment, particles already incorporated into a porous matrix subsequently can be derivatized by covalently bonding with a reactant or by coating with a sorbent that provides the specific ion selectivity.

In another embodiment, polymeric particles can be incorporated into the sheet materials of the invention. Preferably, these particles comprise at least one derivative of polystyrene divinylbenzene, polyacrylates or polymethacrylates or copolymers thereof, and phenol formaldehyde polymers. All of these particles have capability of sorbing or reacting with a specific radionuclide.

A single layer sheet material useful in the present invention, which preferably is a disk, can have a thickness in the range of 0.05 to 5.0 mm, preferably 0.2 to 2.0 mm.

Desirably, the average pore size of the uniformly porous sheet material can be in the range of 0.1 to 10 micrometers. Void volumes in the range of 20 to 80% can be useful, preferably 40 to 60%. Porosity of the sheet materials prepared from polymer pulp can be modified (increased) by including adjuvant hydrophilic or hydrophobic fibers, such as polyacrylonitrile, polypropylene or polyethylene fibers of larger diameter or stiffness which can be added to the mixture to be blended. Fibers can have an average size (diameter) of up to 20 micrometers, and up to an average length of 4 mm; preferably any adjuvant fibers added, for example, to control porosity are non-sorptive. Up to 99 weight percent of the total fiber content can be adjuvants.

In the present invention, PTFE and polymer pulp can be combined to form the sheet material matrix. Polytetrafluoroethylene (PTFE) can be fibrillated in situ to assist in consolidating the pre-formed pulps. Blends of poly(p-phenyleneterephthalamide) (Kevlar™, Dupont) with PTFE can be useful.

In use, the sheet materials of the present invention, which can be supported on a reinforcing member or scrim (e.g., a porous backing), are challenged with a fluid, which preferably is a liquid, comprising at least one radioactive analyte to be extracted. It may be desirable to pre-wet the sheet material, e.g., with water preferably adjusted to the pH of the sample solution, before passing the fluid through the sheet material. The sheet material can be in the form of a disk, pleated cartridge, bag, pillow, disk in a holder, etc. Vacuum or positive pressure can be used to accelerate the flow-through rate of the fluid.

The sheet material can comprise any ion-specific sorptive or reactive particle entrapped in any porous matrix, which matrix is capable of resisting degradation by radioactive emission for a time sufficient to accomplish the method of the invention. Preferred matrices include PTFE, polyolefins, and aramid.

The sorbent particles can be one type of particle or a combination of types of particles, some of which are commercially available. For the analysis of radioisotopes of elements which are most frequently analyzed, the appropriate sorbents can be selected from among materials listed in Table I. Table I does not necessarily constitute a complete list of candidate materials, and no representation is made about these materials being equally effective.

TABLE I

Particularly Preferred Particles for Use in Present Invention Include:

| Material | Particle trade name/ product name | Available from |
|---|---|---|
| Macrocyclic ligands attached to solid support particles, preferably silica | SuperLig ™ | IBC Advanced Technologies P.O. Box 656 Provo, Utah 84603-0656 |
| Bis-tert-butyl-cis-dicyclohexene-18-Crown-6, on Amberchrom ™ polymeric resin or Amberlite ™ polymeric resin support | Sr-Spec ™ | Eichrom Industries, Inc. 8205 S. Cass Avenue Darien, Illinois 60561 |
| Diamyl amylphosphonate on Amberchrom ™ polymeric resin support | U-TEVA-Spec ™ | Eichrom Industries, Inc. 8205 S. Cass Avenue Darien, Illinois 60561 |
| octyl (phenyl)-N,N-diisobutylcarbamoyl-methylphosphine oxide (CMPO) on Amberchrom ™ polymeric resin support | TRU-Spec ™ | Eichrom Industries, Inc. 8205 S. Cass Avenue Darien, Illinois 60561 |
| Modified titanium phosphate | PhTiA ™ | SERAI, Brussels, Belgium |

The sorbents are available as particulate materials. Any of the particulate materials may have a spherical shape, a regular shape, or an irregular shape. Particulate material which has been found useful in the invention has an apparent size within the range of 0.1 to about 200 micrometers, preferably in the range of 0.1 to 100 micrometers, more preferably 0.1 to 30 micrometers, and most preferably 1 to 10 micrometers. It has been found advantageous in some instances to employ particulate materials in two or more particle size ranges falling within the broad range. As an example, particles having an average size in the range of 0.1 to 30 micrometers may be employed in combination with particles having an average size in the range of 1 to 150 micrometers acting as a property modifier.

More than one type of active sorbent or reactive particles useful in the present invention can be used in any proportion, the total sorptive or reactive particles being present in the range of more than 25 up to 100 weight percent of the total weight of particles present, preferably 35 to 100 weight percent, more preferably 50 to 100 weight percent sorbent particles. A useful embodiment comprises a combination of different sorptive or reactive particles for different specific ions. A sheet material of this type is particularly useful in gross alpha/beta determinations. The ratio of sorptive or reactive particles to matrix is preferably in the range of 40:1 to 1:4, more preferably 40:1 to 1:1. Preferably the particles are uniformly enmeshed throughout the sheet material.

It may be desirable in some embodiments to include non-active, diluent particles. Diluent particles include any particle which does not interfere with the method of the invention and provides advantageous properties to the disk. Such particles include, for example, water-swellable and non-water-swellable particles as described in U.S. Pat. No. 5,279,742, col. 5, line 62, to col. 6, line 42. Diluent particles can comprise organic-coated or uncoated inorganic particles in an amount 0 to 75 weight percent of total particulate, preferably 0 to 65 weight percent, and more preferably 0 to 50 weight percent of total particulate present. Diluent particles may include, for example, dyes or pigments which provide for color coding of the sheet material indicating specificity for a given ion.

Diluent particles can also include radiation absorbing particles, for example, lead, to control radiation from passing through to the bottom surface of the sheet material. Such particles have comparatively little effect upon radiation being emitted from the top surface.

When the porous matrix is PTFE, the process of the present invention can be as disclosed, for example, in U.S. Pat. Nos. 4,153,661 and 5,071,610, which are incorporated herein by reference. Specifically, the PTFE composite article of the invention is prepared by mixing the particulate or combination of particulates employed, PTFE and lubricant, until a uniform mixture is obtained. PTFE and lubricant can be added as a PTFE resin emulsion which is commercially available from DuPont. It has been found that to optimize separation techniques in the resultant article, the amount of lubricant in the mixture, or subsequently added lubricant, i.e., water or water-based solvent or organic solvent, should be present in an amount sufficient to be near or to exceed the lubricant sorptive capacity of the particles preferably by at least 3 weight percent up to 200 weight percent. This range can be optimized for obtaining the desired mean pore sizes for different types of particles and for the different types of separations to be performed. PTFE fibrils can have a diameter in the range of 0.025 to 0.5 micrometers and an average diameter less than 0.5 micrometer.

Useful lubricants as well as blending, mixing, and calendering procedures are disclosed in U.S. Pat. Nos. 4,153,661 and 5,071,610.

When the porous matrix is a polymer pulp, sheet materials can be prepared by dispersing the polymer pulp(s) generally with particulate, preferably using a blender, in the presence of a suitable liquid, preferably water, or water-miscible organic solvent such as alcohol or water-alcohol. The dispersion is poured through a fine screen preferably having pores of about 0.14 mm (100 mesh) to provide a wet sheet, which can then be pressed to remove additional liquid. The sheet is then dried, preferably by heating, to provide a dry sheet preferably having an average thickness in the range of about 0.1 mm to less than 10 mm, more preferably 0.2 mm to 9 mm, most preferably 0.3 mm to 5 mm, and even more preferably 0.4 to 3 mm. Up to 100 percent of the liquid can be removed, preferably up to 90 percent. Calendering can be used to provide additional pressing or fusing, when desired. This general method is provided in U.S. Pat. No. 5,026,456, which is incorporated herein by reference. The sheet resembles porous, unglazed paper that may have color, depending upon its components.

Sheet materials comprising Kevlar are particularly useful when radiolytic, hydrolytic, thermal, and chemical stability are desired. In most cases, such materials will exhibit resistance to swelling when exposed to solvents. Advantageously, Kevlar pulp can be blended with polyolefin pulp to provide a moldable or partially thermally fusible fiber to improve physical properties of the sheet material.

U.S. Pat. No. 3,971,373 discloses webs of blown microfibers, preferably polyolefin webs, and particles can be incorporated in such webs by known procedures. Glass and ceramic nonwoven webs are known and particles can be incorporated in such webs as is known in the art, see, for example, WO 93/01494, which is incorporated herein by referenced.

A relationship can exist between particle size of the sorbent or reactive particles and the thickness of the layer in which the extracted isotopes will be concentrated. Smaller sorbent particles can lead to extraction in a thinner surface band while larger particles result in isotopes being concentrated in a thicker band. The pertinent properties of a particle-loaded membrane are discussed in "Investigation of the Kinetic Properties of Particle-Loaded Membranes for Solid-Phase Extraction by Forced Flow Planar Chromatography," Analytical Chemistry, 65(5) March 1993, pp. 588–594.

The ion-specific sorptive or reactive particles preferably are of sufficiently small size, more preferably of at most 20 micrometers, more preferably of at most 10 micrometers, so that concentration of the analyte in a surface band can be accomplished. The thickness of the surface band should be less than that which would result in significant reabsorption (i.e., more than 50%) of the radiation.

Since essentially total extraction of the isotopes by the membrane is a requirement for quantitative determinations, the thickness of the band containing the extracted isotopes desirably is less than the thickness of the membrane. On the other hand, the preferred thickness of the surface band is also a function of the type of emission characteristic for a given isotope. Pore size of the sheet material of the present invention is important in concentrating the radioactive analyte in a surface band of the article.

Small pores can be helpful in concentrating the analyte in a narrow band so as to minimize re-adsorption of alpha and beta particles within the medium. Small pores are favored by increased processing (e.g., calendering) of the medium.

Radioisotopes emitting gamma radiation can be sorbed in or reacted in a relatively thick surface band without resulting in measurable re-absorption of emitted radiation by the disk material. Gamma counts obtained on the side near the surface band are essentially identical to gamma counts obtained at the opposite side of the single layer sheet material or disk.

Counts of beta particles from sorbed or reacted radioisotopes are attenuated when measured on the side of the disk opposite to the surface band as compared to measurements on the side adjacent to the surface band. A preferred thickness of surface band for use with beta-emitting radioisotopes can be at most 300 micrometers, more preferably at most 100 micrometers, most preferably at most 50 micrometers.

Alpha particles emitted by sorbed or reacted radioisotopes show significant re-absorption by the membrane material. Measurements have shown that, in the case of alpha-emitting radioisotopes, the surface band can be at most 150 micrometers thick, more preferably at most 50 micrometers, and most preferably at most 20 micrometers. Typically, alpha particle counts can only be measured from the surface band, because alpha counts on the side of the disk opposite to the surface band are barely above the background level.

The relationship between type of emission, preferred surface band thickness and particle size of the ion-specific sorbent allows one to design an optimum disk for any given radioisotope. For instance, a disk designed to extract an alpha-, beta-, or gamma-emitting isotope may comprise a sorbent specific to such given isotope. The particles are selected so as to efficiently extract a radionuclide in a surface band of a thickness less than 90% of the total thickness of the disk. This ensures no loss of analyte due to breakthrough.

Band thicknesses have been determined empirically as well as by interpolation of data available in the literature, for example, Encyclopedia of Science & Technology, McGraw Hill, 7th ed., vol. 1, p. 417 (1992).

Disks designed for extraction of a mixture of alpha and beta-emitting isotopes, which are commonly called gross alpha/beta samples, may comprise the appropriate mixture of different sorbent or reactive particles. The mixture can comprise small particles specific to the extraction of alpha-emitting isotopes, and can comprise larger particles specific to the extraction of beta-emitting isotopes.

Alpha or beta particles emitted by the extracted radioisotopes can be counted by conventional alpha or beta spectrometry measures, as the case may be. Typically, radiochemical analyses involve sample quantities of one liter. To extract the specific radioisotope to be measured, an isotope-specific extraction disk is placed in a fritted filter vacuum apparatus and the 1-liter sample is drawn through the pre-wetted disk. The time required for extraction of specific radioisotope(s) from the 1-liter sample can vary between 5 and 30 minutes. This is in contrast to the conventional method of repeated pre-concentration, precipitation and extraction chromatography steps, involving several hours of sample preparation time.

The present invention offers significant advantages in efficiency over conventional sample preparation methods.

The extraction disk can then be dried and placed on a planchet. Planchets refer to thin metal containers used in conventional radiochemical analysis. The planchet can be placed directly on the platform inside the drawer of an alpha/beta particle counter. Alpha/beta particle counters typically have four drawers, each capable of holding four planchets. Certain alpha/beta particle counters accommodate disks with a diameter of 5 cm and others of 12.7 cm. The current tests involved extraction disks of 4.7 cm diameter placed on 5 cm diameter planchets.

The planchet rests on a platform inside the drawer, and the platform is raised by a cam up to the detector. The cam provides both the optimum sample-to-detector distance possible and a reproducible geometry (configuration). Each detector type has a specified counting efficiency, which is determined by planchet-detector configuration and other instrument-specific parameters. The counting efficiencies of the Canberra HT1000™ (Canberra Nuclear Products, Meridian, Conn.) alpha/beta particle counter used in these tests is stated as ≧35% for alpha particles and ≧42% for beta particles.

The present invention can be used to quantitatively and qualitatively measure radioactivity emitted by at least one radionuclide extracted from a fluid in a direct mode. The higher the energy of the radiation, the more accurate is the quantitative method of the present invention. A correction factor can be provided using known standards to account for reabsorption of the radiation within the geometry of the disk. Using these factors, quantitative accuracies greater than 80 percent, preferably greater than 90 percent, and more preferably at least 95 percent, can be achieved.

A disk comprising a combination of different ion-specific particles can be used to measure a combination of any of alpha, beta, and gamma particle emissions from extracted analytes. A stack of disks, each comprising a different ion-specific particle, can be used to extract different analytes which subsequently can be individually measured.

The sheet materials of the present invention are particularly useful to make quantitative and qualitative determinations of radioisotopes present in water, soil, and sedimentary samples.

Objects and advantages of this invention are further illustrated by the following examples, but the particular materials and amounts thereof recited in these examples, as well as other conditions and details, should not be construed to unduly limit this invention.

EXAMPLE 1

The following two Examples utilize SPE extraction disks which were designed specifically for use with strontium radioisotopes. Measurements of strontium isotopes are frequently conducted because they provide an indication of the potential for human exposure to man-made nuclear radiation.

Strontium-specific disks were made using a mixture of 5.0 g SuperLig 620 bonded to 8–12 micrometer silica gel particles (IBC Advanced Technologies, Inc., Provo, Utah), 0.555 g of Fluon™ polytetrafluoroethylene (PTFE) (ICI Americas, Inc., Exton, Pa.), and a solution of 2.25 g of isopropyl alcohol in 8.75 g of distilled water.

The ingredients were mixed until the particles were thoroughly wetted and the mass assumed a putty-like consistency. The material was subsequently worked in a rubber milling machine made by Reliable Rubber and Plastic Machinery (North Burgen, N.J.), at a roll temperature of 41° C. (105° F.), a roll speed of 4.9 meters (16 feet) per minute and roll gap of 0.15 cm (0.060 inches). The putty-like material was passed through the nip of the mill in an initial pass, folded, then passed through the nip progressively reducing the roll gap from 0.15 cm to 0.05 cm to form a membrane sheet. After drying the membrane in an oven at 66° C. (150° F.) for 60 minutes, disks of 47 mm diameter were punched out of the membrane. The final dried strontium-specific disks contained SuperLig 620 particles to PTFE in the range of 90 parts to 10 parts by weight and had a thickness of about 100 micrometers. Details of this preparation process are disclosed in U.S. Pat. No. 5,071,610.

Strontium test solutions were made as follows:

One mL of a standard strontium solution containing 0.006 mg of stable strontium ion and about 1500 dpm (disintegrations per minute) of strontium$^{89}$ as the nitrate in water was added by a pipette to 126 mL of concentrated nitric acid (15.8 molar). Distilled or tap water, as indicated in Table II, below, was added to make one liter of strontium test solution. Where indicated in Table II, 0.004 mg additional stable strontium was added to challenge the capacity of the disk to sorb strontium ions.

Extractions were made as follows:

Extractions were performed by placing a 47 mm strontium-specific disk in a conventional 50 mm fritted filter vacuum apparatus. The disk was wetted prior to sample extraction by drawing 2 mL of methanol through the disk under moderate vacuum conditions. This was followed by drawing a 20 mL rinse of 2 molar nitric acid through the disk. Each sample listed in Table II was prepared by then drawing one liter of the strontium test solution through the disk. The beta count from the strontium bound to the particles in the disk was measured directly from the disk as described in the beta counting technique procedure below.

The possibility of breakthrough of the strontium solution was ruled out by comparing the beta activity of the initial and the filtrate solutions as is described below.

The procedure used as the beta counting technique was as follows:

a) Equipment used: Canberra™ AT1000 low background gas flow proportional counter;

b) Disks of 47 mm diameter were placed on a 50 mm planchet and positioned in the instrument. Similarly, reference samples and planchets containing filtrate precipitates were placed in the instruments;

c) The beta counts from each sample were measured for a set period of time;

d) Calibration: the detection efficiency of the system was calculated for each geometry (detector-planchet configuration) by comparison of the sample concentrate with that of a known quantity of $Sr^{89}$ incorporated into a geometry similar to that of the sample.

The filtrate was prepared for beta counting as follows:

The possibility of breakthrough of the strontium solution was ruled out by comparing the beta activity of the initial and the filtrate solutions. The beta count from the strontium in the filtrate was determined by precipitation as strontium carbonate following the addition of a known quantity of a solution of nonradioactive strontium.

To a 200 mL aliquot of the filtrate, 40 mg of nonradioactive strontium was added as 4 mL of 10 mg strontium per mL nitrate solution. This was made basic by the addition of 10 molar sodium hydroxide sufficient to precipitate strontium carbonate upon the addition of 5 mL of saturated sodium carbonate solution. The precipitate was alternately washed with dilute sodium hydroxide and centrifuged. The solid was transferred to a 50 mm planchet and dried under an infrared heat source or rinsed with acetone and allowed to air dry.

Using the beta counting technique described above, the beta count rate of the precipitate was measured and the $Sr^{89}$ activity as dpm per liter was calculated. The strontium bound in the disk was measured directly and, where indicated, compared to that calculated by the difference between the original activity of solution and that found in the filtrate. Results are reported in Table II.

test solution for about 12 hours. When removed, dried, and beta count activity measured, about one-half of the radioactive strontium was found to be sorbed in each of the disk surface bands. Note the substantially equal distribution between the top and the bottom in both samples.

Disks 11 and 12 were stacked together to demonstrate the efficiency by which the disks removed the strontium. Disk 12 was placed under and in direct contact with disk 11 in the fritted filter. One liter of the strontium solution was passed through the stack of two disks which were then separated, dried, and the beta count activity measured. The experiment demonstrated that substantially all the strontium was absorbed in the top disk, more specifically, in the top band of the top disk. This experiment also demonstrates that it can be useful to provide disk 12 with a different ion-specific particle that can extract a second radionuclide, cesium for example, in the same process. Radioactivity counts of other ions, such as U, Pu, Ra, and Am, can be similarly measured after they are sorbed from a fluid on disks containing ionic specific particles. Further, a third, fourth, or more disks can be stacked and a sequence of radionuclides can be extracted on separate disks. The disks can be separated from each other and their emitted radiation measured separately.

EXAMPLE 2

This example refers to the extraction of strontium isotopes in the presence of a variety of other radionuclides. In order

TABLE II

Strontium Radioisotope Samples

| Disk | Sr test solution dpm | Min. to flow one liter | Water use for test solution(a) | Sr added(e) | Drying method | Top of disk(b) | Bottom of disk(c) | Filtrate(d) |
|---|---|---|---|---|---|---|---|---|
| 1 | 1,270 | 18 | DI | 0 | oven | 99 | 86 | 1.2 |
| 2 | 1,270 | 16 | DI | 0 | acetone | 100 | 84 | —(f) |
| 3 | 1,270 | 15 | DI | 0 | oven | 100 | 88 | 1.2 |
| 4 | 1,270 | 14 | DI | 0 | oven | 97 | 88 | — |
| 5 | 1,299 | 12 | DI | 0.004 | acetone | 101 | 89 | — |
| 6 | 1,299 | NR | DI | 0.004 | acetone | 96 | 86 | — |
| 7 | 1,299 | 30 | tap | 0 | acetone | 107 | 91 | — |
| 8 | 1,299 | 14 | tap | 0 | acetone | 106 | 91 | 10.1 |
| 9 | 1,299 | 12 hours | DI | 0 | oven | 49 | 48 | — |
| 10 | 1,299 | 12 hours | DI | 0 | oven | 48 | 48 | — |
| 11 | 1,299 | 28 | DI | 0.004 | acetone | 98 | 87 | — |
| 12 | N/A(g) | 28 | DI | 0.004 | acetone | 0.1 | 0 | 1.2 |

(a)DI = deionized water; tap = tap water
(b)percent of initial radionuclide measured from top surface band of disk
(c)percent of initial radionuclide measured from bottom surface band of disk
(d)percent of initial radionuclide found in filtrate
(e)mg nonradioactive Sr added to test solution
(f)— means not measured
(g)not applicable In Table II, top of disk refers to the count from the top of the disk, that is, the surface first contacted by the strontium test solution. This surface was placed "up" on the planchet and the beta particle count determined. The beta count was determined on the bottom of the disk by turning the disk over on the planchet and repeating the counting.

Disks 1–8 in Table II show almost identical results under varying conditions. Within the accuracy of the counter close to 100% the radioactive nuclides from the test solution were isolated on the disk and their emitted radiation was measurable from the top band. The measurement taken on the bottom of the disk showed minor loss of activity of approximately 10–15 percent.

Disks 9 and 10 demonstrate another application of this technology. Rather than passing the solution through the disk, each disk was suspended (immersed) in the strontium to demonstrate the usefulness of a strontium-specific sample preparation, the disk would need to efficiently extract strontium without extracting any other radionuclides that might interfere with the beta count attributable to the strontium.

A test solution was prepared by dissolving 0.78 grams of standard diluted pitchblende in mineral acids, evaporating to dryness and redissolving in 1 liter of deionized water. The solution was passed through a Whatman 42 filter paper to remove undissolved solids. The pitchblende contained natural uranium and associated progeny, including isotopes of uranium, thorium, and radium. One hundred mL of the pitchblende solution which corresponded to a gross beta activity of 185 dpm and an amount of radioactive strontium$^{89}$ corresponding to 1424 dpm, and 127 mL of 2M nitric acid were diluted to 1 liter with deionized water.

A strontium-specific disk, such as described in Example 1, was placed in a 50 mm fritted filter vacuum apparatus. After having been wetted with 2 mL of ethanol, the disk was rinsed with 20 mL of 2M nitric acid. The 1 liter solution from above was passed through the disk. The disk was air-dried after having been rinsed with 2 mL of acetone. The disk was then used to determine the beta particle count from the top band and from the bottom of the disk using the procedure described in Example 1. The beta count from the top band corresponded to 99.3% of the activity of the initial strontium test solution and from the bottom of the disk corresponded to 88%. The disk exhibited no measurable contamination from potentially interfering beta emitters originating from non-strontium components of the pitchblende solution.

This example represents the specific extraction and accurate representation of strontium isotopes in the presence of various, potentially interfering radionuclides at a level of dissolved solids approximately 150 mg/liter.

EXAMPLE 3

This example shows quantification of $Cs^{137}$ from a solution which also comprised other ionic species including radioactive strontium.

Disks for this example were prepared as described in Example 1 with the substitution of 5.0 g of PhTiA™ (SERAI, Brussels, Belgium), a titanium phosphate modified mineral particle ground to 10 to 50 micrometers. PhTiA is a cesium specific separation particle. In this example, the disks were cut to 22 mm diameter.

For this example, a test solution containing $cesium^{137}$ at a concentration equivalent to 3.3 million dpm (disintegrations per milliliter) or about 1 mg/liter, $strontium^{90}$ at 3.1 million dpm or about 1 mg/liter, lead at 300 mg/liter, sodium at 33 mg/milliliter, potassium at 7 mg/milliliter and many other nonradioactive ions at lower concentrations was used.

In a radiation laboratory cell provided with proper shielding and through the use of micromanipulators, two disks prepared as described above were placed in threaded in-line plastic holders and the two holders equipped with a feed tube connected together in series. A peristaltic pump was connected to the feed tube and used to pump deionized water from a reservoir and through the pair of disk holders. This was followed by pumping a few mL of a wash solution of 0.5M nitric acid through the disks. 16 mL of the test solution described above was pumped through the disks at a rate of about 1 to 2 mL per minute, allowing the particle to sorb the cesium. The other ions present were allowed to pass through as part of the filtrate and passed into a collection vessel.

The collection vessel containing the filtrate was placed in an Ortec Spectrum Master, Model 92X Spectrometer (EG&G Nuclear Instruments, Oak Ridge, Tenn.) and the gamma radiation was measured to be 8670 dpm, about 0.2 percent of the value of the original test solution, or by inference 99.8% of the radioactive cesium became sorbed on the disks. The beta radiation for strontium in the filtrate was measured in a similar fashion and found to be 2.9 million dpm or about 94% of the radiation of the original test solution. These result indicated very little sorption of $strontium^{90}$ on the disks and that almost all radiation measured directly from the disk surface would be attributable to the radioactive cesium.

To verify the presence of radiation emitted from the disks, all liquid was swept out of the tubes and holders and the two holders were disconnected from the tubing. Using the micromanipulators, the holders were held up against a permanently installed Ortec Spectrum Master, Model 92X Spectrometer in the radiation cell and gamma radiation of over two million dpm was indicated. The disk holders were then placed on the benchtop and the radiation of the micromanipulator assembly only was measured. The results were several orders of magnitude lower showing that significant radiation emanated from the disks and not from the micromanipulator assembly.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A solid phase extraction sheet material comprising ion-specific sorptive or reactive particles and a porous matrix as carrier for said particles, said sheet material further comprising a radioactive analyte bound to said particles which is the same as said specific ion, said analyte emitting at least one of alpha, beta, and gamma radiation, said analyte being concentrated in a surface band of thickness less than that which would result in readsorption of more than 50 percent of the radiation and being analyzable in a direct mode for at least one of quantitative and qualitative data relating to said radioactive analyte.

2. The solid phase extraction sheet material according to claim 1 which is a single layer sheet material.

3. The solid phase extraction sheet material according to claim 2 wherein said analyte emits alpha radiation and is concentrated in a surface band of said sheet material which is more than 0 and up to 150 micrometers thick, provided that the band is at most 90 percent of the thickness of the single layer sheet material.

4. The solid phase extraction sheet material according to claim 2 wherein said analyte emits beta radiation and is concentrated in a surface band of said sheet material which is more than 0 and up to 300 micrometers thick, provided that the band is at most 90 percent of the thickness of the sheet material.

5. The sheet material according to claim 1 wherein said ion-specific particles are enmeshed in said porous matrix carrier.

6. The sheet material according to claim 1 wherein said ion-specific particles are located on at least one surface of said carrier.

7. The solid phase extraction sheet material according to claim 1 wherein said porous matrix comprises a fibrillated polymer.

8. The solid phase extraction sheet material according to claim 1 wherein said porous matrix comprises nonwoven fibers.

9. The solid phase extraction sheet material according to claim 1 wherein said porous matrix comprises a fibrous polymer pulp.

10. The solid phase extraction sheet material according to claim 1 wherein said porous matrix comprises a fibrous polymer blend.

11. The solid phase extraction sheet material according to claim 8 wherein said nonwoven fibers are selected from the group consisting of polyolefins, copolymers of polyolefins, aramids, glass, and ceramics.

12. The solid phase extraction sheet material according to claim 11 wherein said polyolefins or copolymers thereof are selected from the group consisting of polypropylene, polyethylene, and polyacrylonitrile.

13. The solid phase extraction sheet material according to claim 11 wherein said polyolefin is polytetrafluoroethylene.

14. The solid phase extraction sheet material according to claim 11 wherein said aramid is a poly(p- or m-phenyleneterephthalamide) or a chemical modification thereof.

15. The solid phase extraction sheet material according to claim 1 wherein said sorptive or reactive particles are derivatives of an inorganic oxide.

16. The solid phase extraction sheet material according to claim 15 wherein said inorganic oxide is selected from the group consisting of silica, alumina, titania, and zirconia.

17. The solid phase extraction sheet material according to claim 15 wherein a macrocyclic ligand is covalently bonded to said inorganic oxide.

18. The solid phase extraction sheet material according to claim 15 wherein a long-chain ligand is covalently bonded to said inorganic oxide.

19. The solid phase extraction sheet material according to claim 1 wherein said particles are selected from the group consisting of bis-tert-butyl-cis-dicyclohexene-18-Crown-6 on a polymeric resin support, diamyl amylphosphonate on a polymeric resin support, and octyl(phenyl)-N,N-diisobutylcarbamoylmethylphosphine oxide on a polymeric resin support.

20. The solid phase extraction sheet material according to claim 1 wherein said sorptive or reactive particles are modified titanium phosphate.

21. The solid phase extraction sheet material according to claim 1 wherein said sorptive or reactive particles comprise a combination of sorptive or reactive particles specific to different ions.

22. The solid phase extraction sheet material according to claim 1 which further comprises diluent particles.

23. The solid phase extraction sheet material according to claim 22 wherein said diluent particles comprise a pigment or dye.

24. The solid phase extraction sheet material according to claim 22 wherein said diluent particles are radiation absorbers.

25. The solid phase extraction sheet material according to claim 1 which is a disk.

26. The solid phase extraction sheet material according to claim 1 which comprises a stack of disks, each disk being a solid phase extraction sheet material comprising sorptive or reactive particles specific to a different ion.

27. The solid phase extraction sheet material according to claim 25 wherein said disk has a thickness in the range of 0.05 to 5.0 mm.

28. The solid phase extraction sheet material according to claim 1 wherein the ratio of said ion-specific particles to porous matrix is in the range of 40:1 to 1:4 by weight.

29. A method for providing a sheet material comprising a radiochemical analyte comprising the steps of:
   a) providing a solid phase extraction sheet material comprising ion-specific sorptive or reactive particles and a porous fibrous nonwoven matrix as carrier for said particles, and providing a fluid including a radiochemical analyte comprising the specific ion, and
   b) passing said fluid through said sheet material in a single pass, said particles selectively extracting said analyte from said fluid, the analyte being concentrated in a surface band having a thickness less than that which would result in readsorption of more than 50 percent of the radiation.

30. The method according to claim 29 wherein said surface band has a thickness less than 90 percent of the total thickness of said sheet material.

31. The solid phase extraction sheet material according to claim 1 wherein said surface band has a thickness less than 90 percent of the total thickness of said sheet material.

* * * * *